United States Patent [19]

Elsasser et al.

[11] Patent Number: 5,183,908

[45] Date of Patent: Feb. 2, 1993

[54] PROCESS FOR THE PREPARATION OF SUBSTITUTED FURANONES

[75] Inventors: A. Frederick Elsasser; Thomas J. Korte, both of Cincinnati, Ohio

[73] Assignee: Henkel Corporation, Ambler, Pa.

[21] Appl. No.: 485,821

[22] Filed: Feb. 27, 1990

Related U.S. Application Data

[63] Continuation of Ser. No. 191,443, May 9, 1988, abandoned, which is a continuation-in-part of Ser. No. 944,149, Dec. 19, 1986, abandoned.

[51] Int. Cl.$^5$ ............................................. C07D 307/20
[52] U.S. Cl. ........................................ 549/322; 549/295
[58] Field of Search ........................................... 549/322

[56] References Cited

FOREIGN PATENT DOCUMENTS 546573 9/1957 Canada ................................. 549/322
12662 7/1967 Japan ..................................... 549/322

*Primary Examiner*—Carolyn Elmore
*Assistant Examiner*—Mark W. Russell
*Attorney, Agent, or Firm*—Ernest G. Szoke; Wayne C. Jaeschke; Henry E., Millson, Jr.

[57] ABSTRACT

This invention relates to an improved process for the preparation of 3-acyl-5-alkyldihydro-2(3H)-furanones according to the following reaction scheme:

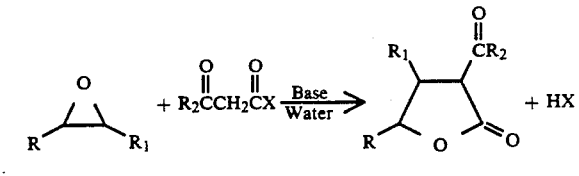

wherein R and $R_1$ are hydrogen or alkyl and $R_2$ is a hydrocarbon or -O-hydrocarbon radical of from 1 to 20 carbon atoms and X is a leaving group.

4 Claims, No Drawings

PROCESS FOR THE PREPARATION OF SUBSTITUTED FURANONES

This application is a continuation of application Ser. No. 07/191,443 filed on May 9, 1988 now abandoned, which is a continuation-in-part of application Ser. No. 944,149, filed on Dec. 19, 1986 now abandoned.

BACKGROUND OF THE INVENTION

1. Field of the Invention

This invention relates to an improved process for the preparation of lactones and, more specifically, substituted furanones of the formula:

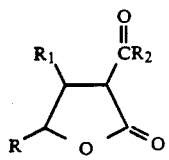

wherein R and $R_1$ are hydrogen or alkyl and $R_2$ is a hydrocarbon radical or -O-hydrocarbon radical.

2. Description of the Prior Art

Johnson U.S. Pat. No. 2,433,827, describes the preparation of alpha-acetyl-gamma-butyrolactone [3-acetyl-dihydro-2(3H)-furanone] by reacting ethylene oxide with ethyl acetoacetate in an ethanol solution of an alkali metal hydroxide in which the temperature during the reaction is maintained between 0° C. and −5° C. for 48 hours and thereafter recovering the alpha-acetyl-gamma-butyrolactone by extraction and subsequent fractionation. The yield of the desired lactone is stated to be of the order of 60% but in actual practice has been found to be considerably lower. The Johnson process also suffers from the disadvantage of requiring operating temperatures of not higher than 0° C. for a time period of at least 48 hours.

Noting the unduly prolonged reaction times required at temperatures below 0° C., Lacey et al in Canadian Patent No. 546,573 disclose a process for the production of alpha-aceto-gamma-lactones by reacting an epoxide with an acetoacetate of a $C_{4-6}$ tertiary alkanol at temperatures from −10° C. up to +10° C. Temperatures of 0° C. to +3° C are indicated to be preferred. Lacey et al further specify that the reaction is carried out by adding either a mixture of the reactants to aqueous alkali or by first forming the sodium derivative of the acetoacetate and adding the epoxide thereto.

It would be highly desirable if it were possible to carry out the reaction at even higher temperatures for shorter periods of time while at the same time significantly increasing the yield of the desired lactone product. These and other advantages are readily achieved by the improved process of the present invention.

SUMMARY OF THE INVENTION

The present invention relates to a process of preparing substituted furanones according to the following reaction scheme:

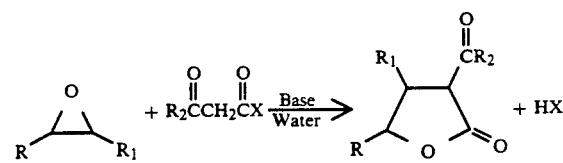

wherein R, $R_1$, and $R_2$ have the meanings hereinbefore defined and X represents a leaving group. The reaction is preferably conducted in an aqueous solution of sodium hydroxide or potassium hydroxide. Furanone derivatives produced by the process have highly desirable odor characteristics which render them useful in fragrance applications. In a particularly useful embodiment of this invention wherein high yields of the substituted furanones are obtained, the reaction is carried out by introducing a base and water into a mixture of the epoxide and beta-diketo compound at a rate such that the temperature of the reaction mixture does not exceed 40° C. and then maintaining the temperature from 0° C. to 40° C. until the reaction is essentially complete whereupon the mixture is acidified, the organic phase separated, and the substituted furanone product recovered therefrom. It is especially useful when the epoxide is a 1,2-epoxyalkane and the beta-diketo compound is a beta-ketoester wherein the ester moeity is derived from an aliphatic alcohol having from 4 to 10 carbon atoms.

DETAILED DESCRIPTION OF THE INVENTION

The present invention relates to a novel process of preparing substituted furanones of the formula:

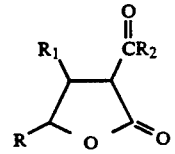

wherein R and $R_1$ are hydrogen or $C_{1-8}$ alkyl and $R_2$ is a $C_{1-20}$ hydrocarbon radical or -O-hydrocarbon radical having from 1-20 carbon atoms. Suitable -O-hydrocarbon groups include alkoxy, cycloalkoxy and aryloxy groups. Preferably $R_2$ will contain from 1 to 12 carbon atoms. Particularly useful lactones of this invention are those wherein $R_1$ is hydrogen and R and $R_2$ are alkyl groups.

The furanones are prepared by reacting an epoxide of the formula

wherein R and $R_1$ have the meanings hereinbefore given with a beta-diketo compound, e.g., ketoester or diester, of the formula

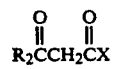

wherein $R_2$ is a $C_{1-20}$ hydrocarbon radical or -O-hydrocarbon radical having from 1 to 20 carbon atoms and X is a leaving group, preferably a $C_{1-12}$ alkoxy group. In an especially useful embodiment of this invention, $R_2$ is a $C_{1-4}$ alkyl group.

Useful epoxides for the process include ethylene oxide and higher epoxides having a single terminal or internal epoxy group. Especially useful substituted lactones are produced when the epoxide is a 1,2-epoxyalkane, i.e., $R_1=H$ and $R=C_{1-8}$ alkyl and, more preferably, $C_{1-4}$ alkyl. Suitable 1,2-epoxyalkanes which may be used in the present process include ethylene oxide, 1,2-butylene oxide, 1,2-propylene oxide, 1,2-pentylene oxide, 1,2-epoxy-5-hexene, and 1,2-hexylene oxide.

Suitable beta-diketo compounds which can be employed for the process include ketoesters, diketones and diesters, such as, ethyl acetoacetate, n-propyl acetoacetate, isopropyl acetoacetate, n-butyl acetoacetate, t-butyl acetoacetate, sec-butyl acetoacetate, n-hexyl acetoacetate, 2-ethylhexyl acetoacetate, n-octyl acetoacetate, isooctyl acetoacetate, isodecyl acetoacetate, and the like.

The reaction is carried out in the presence of water and a suitable base such as those of the group IA metals, preferably, sodium, potassium, or lithium. For the improved process of this invention, which results in improved yields of the desired furanone products with improved reaction rates and minimal by-product formation, the epoxide and beta-diketo compound are first combined and the base subsequently added thereto. The addition of the base is carried out in a manner to insure intimate contact with the reactants. Typically, suitable agitation is employed or the reaction mixture is circulated using a suitable pump or the like. The rate of addition of the base is controlled so that the temperature of the reaction mixture does not exceed 40° C.

The molar ratio of the epoxide to beta-diketo compound can range from about 1:1 to 1:3. More preferably, the molar ratio of these reactants range from 1:1.1 to 1:1.7. A slight molar excess, based on the beta-diketo compound of base is typically employed for the reaction. While molar excesses of up to about 5% base can be employed, based on the beta-diketo compound, 2% to 4% molar excess is most typically used.

For the addition, it is preferred to use aqueous solutions of the base. Such solutions are conveniently added to the mixture of the epoxide and beta-diketo compound. Aqueous solutions of sodium hydroxide and potassium hydroxide are particularly useful for this purpose. While it is not essential, water may be included with the epoxide and beta-diketo compound prior to addition of the base. This is often advantageous and facilitates mixing and temperature control.

In general, sufficient water should be included in the reaction, either by direct addition to the epoxide/beta-diketo compound or upon addition of an aqueous base solution, so that a homogeneous reaction mixture is obtained and salts formed during the course of the reaction are solubilized. To accomplish this, the amount of water in the reaction mixture will usually range from about 20% to 60% by weight. Most generally from 25% to 40% water, based to the total reaction mixture, is employed.

After the base has been added to the epoxide and beta-diketo compound, the mixture is maintained at a temperature from about 0° to 40° C. until the reaction is essentially complete. This can be conveniently accomplished by determining the amount of the limiting reactant remaining in the reaction mixture by gas chromatographic procedures or the like. Reaction times will vary depending on the reactants used and reaction conditions, however, they generally are less than 16 hours and, more usually, on the order of 10 hours or less. It is particularly advantageous for the present process to maintain the reaction at a temperature from about 20° C. to 35° C. when addition of the base is completed and until the reaction is terminated.

When the reaction is substantially complete, the mixture is neutralized by the addition of a suitable acid to a pH of 7 or below. While mineral acids are preferred for the neutralization, organic acids may also be employed. The amount of acid required will, of course, vary depending on the particular acid and the amount of base employed for the reaction. Useful mineral acids which can be used for the neutralization include nitric acid, sulfuric acid, hydrochloric acid, and hydrobromic acid. Hydrochloric acid has been found to be particularly useful for the neutralization. Suitable organic acids include formic acid, acetic acid and the like. Most generally, the pH after neutralization will be between about 4 and 7.

After neutralization the mixture is allowed to stand until the aqueous and organic phases have separated. The organic phase containing the lactone product is then removed from the aqueous phase which contains the water soluble salts formed during the reaction. The furanone derivative (lactone) is then recovered from the organic phase using conventional techniques. If the product is to be further reacted, as is the case when it is used as an intermediate for the preparation of dihydrofuran fragrance chemicals, it may be sufficient to simply "strip off" the alcohol at an elevated temperature and under reduced pressure. In other instances, the product may be fractionally distilled to obtain the desired furanone derivative in higher purity.

Whereas the leaving group X of the beta-diketo compound can include a variety of -O-hydro-carbon radicals, such as alkoxy, cycloalkoxy, aryloxy, and the like, in one preferred embodiment of this invention, the beta-diketo compound is a beta-ketoester wherein X is an alkoxy group containing from 4 to 10 carbon atoms. With such ketoesters, the corresponding $C_{4-10}$ aliphatic alcohol is formed as the reaction proceeds. The resulting furanone derivatives ar readily soluble in these alcohols and, in addition, upon acidification the alcohols facilitate separation of the organic and aqueous phases. The $C_{4-10}$ alkoxy group can be straight-chain or branched-chain and the oxy moiety can be located on a primary, secondary or tertiary carbon. It is especially advantageous to utilize beta ketoesters wherein the alkoxy group contains from 5 to 8 carbon atoms, particularly, if the alkoxy group is a branched-chain alkoxy. These provide very rapid phase separation, high product yields, and the corresponding alcohols have a boiling point such that they can be readily separated from the furanone. Particularly useful furanone products are obtained by the present process when $R_2$ of the above-identified beta-ketoesters is a $C_{1\alpha}$ group and the ketoester is reacted with a 1,2-epoxyalkane having from 3 to 6 carbon atoms, i.e. where $R_1=H$ and R is a $C_{1-4}$ alkyl.

In a particularly useful embodiment of this invention, a process is provided for preparing substituted furanone which comprises combining a 1,2-epoxyalkane containing from 3 to 6 carbon atoms, a beta-diketoester of the formula

where $R_2$ is a $C_{1-4}$ alkyl group and X is a $C_{4-10}$ alkoxy group, and water; adding aqueous sodium hydroxide or potassium hydroxide with agitation at a rate such that the temperature of the reaction mixture does not exceed 40° C., said reaction mixture containing 20% to 60% water and 2% to 4% molar excess of the base, based on the beta-diketoester, with the molar ratio of the 1,2-epoxyalkane to beta-diketoester ranging from 1:1.1 to 1:1.7; maintaining the temperature of the mixture from 20° C. to 35° C. until the reaction is essentially complete; adding mineral acid to adjust the pH to between 4 and 7; separating the organic phase from the aqueous phase and recovering therefrom a substituted furanone product of the formula

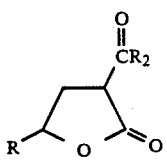

wherein R is a $C_{1-4}$ alkyl group and $R_2$ is the same as defined above. It is even more advantageous when, in the above-described embodiment, the 1,2-epoxyalkane is 1,2-butylene oxide or 1,2-pentylene oxide.

A variety of useful furanone derivatives can be obtained by the improved process of this invention. Furanones are useful fragrance chemicals and they are also useful as chemical intermediates. A particularly useful furanone derivative which can be produced by the process is 3-acetyl-5-butyldihydro-2(3H)-furanone. This compound has highly desirable odor characteristics and is useful in a variety of fragrance formulations.

The invention will be described in greater detail in conjunction with the following specific examples in which the parts are by weight unless otherwise specified.

EXAMPLE I

Preparation of 3-Acetyl-5-Ethyldihydro-2(3H)-Furanone

Sodium hydroxide (42 g/200 ml water) was charged to a 500 ml flask equipped with a mechanical stirrer, addition funnel, condenser, ice bath, and pot thermometer. The mixture was cooled to 15° C. and ethyl acetoacetate (130 g, 1.0 mole) was slowly added below 20° C. over two hours. The mixture was stirred an additional ½ hour at 15° C. 1,2-Butylene oxide (107 g, 1.5 moles) was added over 1½ hours. The reaction was followed by gas chromatography (GC) in the standard manner.

The mixture was allowed to stand overnight and was transferred to a separatory funnel and acidified with 125 ml concentrated hydrochloric acid. The organic layer was separated and the water layer extracted three times with 50 ml diethyl ether. The extracts were combined with the organic layer, dried through sodium sulfate, and the diethyl ether was removed by means of a Rotovap. 182 Grams of product were obtained which when analyzed by GC indicated 83.6% lactone and 7.8% ethyl acetoacetate.

The mixture was distilled using a short adiabatic column and a short path head. A first fraction (28.4 g) boiling below 95° C. at 1.8 torr was collected which contained 3.4% of lactone when analyzed by gas chromatography. A second fraction (93.0 g) having a boiling point of 95-100° C. at 1.8 torr contained 95% of the desired lactone product

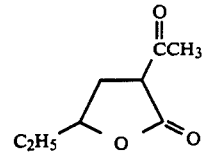

when analyzed by gas chromatography (yield 57%).

EXAMPLE II

Preparation of 3-Acetyl-5-Ethyldihydro-2(3H)-Furanone

Sodium hydroxide (150 g/750 g water) was charged to a 2-liter flask equipped with a high efficiency mechanical stirrer, condenser, cooling bath, pot thermometer and addition funnel. The mixture was cooled to 15° C. and ethyl acetoacetate (480 g, 3.7 moles) was slowly added. After 25 g of ethyl acetoacetate had been added, the mixture became very thick and the remaining ethyl acetoacetate was mixed with 1,2-butylene oxide (350 g, 4.8 moles) and the combination slowly added to the pot below 15° C. The addition took 2½ hours. The reaction was stirred and followed by GC in the standard manner. The mixture was allowed to stand overnight.

115 Milliliters (210 g) concentrated sulfuric acid was added to the pot while maintaining the temperature below 25° C. (cooling was necessary) over ¼ hour. The mixture was acidic. The mixture was transferred to a separatory funnel and sufficient hot water (approx. 2 liters) was added to dissolve the salts. The product was extracted with diethyl ether, dried through sodium sulfate, and the diethyl ether was removed by means of a Rotovap. The crude material was distilled and purified using a Raschig ring packed column and a Perkins Triangle Head. Upon distillation, 16.2 g of a first fraction boiling below 96° C. at 2.0 torr and 337.0 g of a second fraction having a boiling point of 95-100° C. at 2.0 torr and containing 91.5% of the furanone product (yield 54%) were obtained.

EXAMPLE III

Preparation of 3-Acetyl-5-Ethyldihydro-2(3H)-Furanone

Sodium hydroxide [554 g (13.85 moles) in 2 kg water] was charged to a 12 liter flask equipped with a mechanical stirrer, water bath, pot thermometer, addition funnel, and condenser. Ethyl acetoacetate (1640 g, 12.62 moles) and 1,2-butylene oxide (1000 g, 13.88 moles) were mixed and charged to the addition funnel. The addition to the flask took about 2½ hours at a temperature of about 20° C. After stirring 5 hours below 35° C. hydrochloric acid (1200 g, 13.85 moles) was added over a period of 45 minutes at a temperature below 25° C. After settling for 15 minutes, the bottom (aqueous) layer was separated from the top (organic) layer.

The water layer was extracted three times with diethyl ether, the extracts were combined and dried through sodium sulfate and the diethyl ether was removed by means of a Rotovap giving 122 g of product which when analyzed by gas chromatography comprised 21% lactone.

The organic layer was stripped using an aspirator vacuum (60 mm) and heating the flask to 60° C. leaving a net residue of 618 g. The residue was distilled using a packed column and Perkins Triangle Head. The product obtained by distillation comprised three fractions, 164 g, 130 g, and 114 g, respectively, comprising mostly ethyl acetoacetate. The pot material was filtered and the distillation continued to obtain 16.1 g of a fourth fraction boiling below 105° C. at 5 torr that comprised 8% lactone and 887 g of a fifth fraction having a boiling point of 110–120° C. at 5 torr that comprised 92.5% of the desired product when analyzed by gas chromatography. Yield of lactone (fifth fraction) was 42%.

EXAMPLE IV

Preparation of 3-Acetyl-Dihydro-2(3H)-Furanone

Sodium hydroxide (100 g/400 g water) was charged to a one liter flask equipped with a mechanical stirrer, ice bath, thermometer, addition funnel, and condenser. Ethyl acetoacetate (325 g, 2.5 moles) was charged to the additional funnel and the flask cooled to 5° C. Ethylene oxide (120 g, 2.7 moles) was condensed into the addition funnel and the mixture added to the flask below 15° C. over a period of four hours. The mixture was a thick white slurry. After one hour gas chromatography showed an 86:14 ratio of ethyl acetoacetate to product. After 2½ hours the ratio was 80:20. The mixture was stored in the freezer overnight.

After warming the mixture to about 20° C. and stirring for 15 minutes, a sample showed 13.6% ethylene glycol, 38.3% ethyl acetoacetate, and 39.8% product by gas chromatography. The material was left to stir. After one hour the temperature of the mixture had risen to 24° C. and when analyzed showed no ethylene glycol, 70.7% ethyl acetate, and 23.6% product. The mixture was cooled to 20° C. and 30 g more of ethylene oxide were added. After one hour of stirring the temperature had risen to 24° C. and when analyzed by gas chromatography showed 15.4% ethylene glycol, 20.7% ethyl acetoacetate, and 50.9% product. After stirring for one hour the mixture was neutralized with 70 ml of concentrated sulfuric acid below 20° C. Water was added to dissolve the salts and the product extracted with diethyl ether. The extracts were combined and dried over sodium sulfate. The material was filtered and the diethyl ether was removed by means of a Rotovap at 50° C. and aspirator vacuum leaving 247 g of crude product.

The mixture was distilled using a Raschig ring packed column and a Perkins Triangle Head. Seven fractions were obtained and analyzed by gas chromatography. Fractions 1–3 were found to be principally ethyl acetoacetate. Fraction 4 analyzed 11% ethyl acetoacetate and 42% of the desired lactone. Fractions 5 and 6 showed 98.4% lactone and 95.4% lactone, respectively. The yield of the desired lactone product

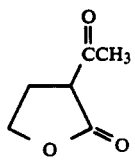

(fractions 5 and 6) was 32%.

EXAMPLE V

Preparation of 3-Acetyl-5-Methyldihydro-2(3H)-Furanone

Sodium hydroxide (100 g/400 g water) was charged to a one liter, four-neck flask equipped with an ice bath, mechanical stirrer, dry ice condenser, pot thermometer, and addition funnel. Ethyl acetoacetate (325 g, 2.5 moles) and propylene oxide (174 g, 3.0 moles) were mixed and charged to the addition funnel. The pot was cooled to 15° C. and the ethyl acetoacetate-propylene oxide mixture was added below 20° C. over a period of two hours. The reaction was followed by GC in the standard manner.

After six hours the mixture was transferred to a two liter separatory funnel and acidified with 225 ml of concentrated hydrochloric acid. The two layers were separated and the lower aqueous layer extracted three times with diethyl ether. The extracts were combined with the original organic layer, dried over sodium sulfate, and the diethyl ether was removed by means of a Rotovap at 70° C. at aspirator pressure.

The material was distilled using a packed column and a Perkins Triangle Head. Fractions 1–3 (94 g) contained mostly ethyl acetoacetate. A fourth fraction (170 g) boiling point at 112–117° C. at 7 torr contained essentially 100% lactone when analyzed by gas chromatography. The pot residue was then short path distilled and 22 g of material having a boiling point of 110° C. at 6 torr that comprised 89% lactone when analyzed by gas chromatography was obtained. Yield of lactone of the desired lactone

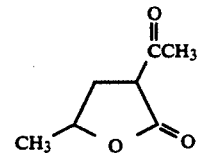

was 53%.

EXAMPLE VI

Preparation of 3-Acetyl-5-Ethyldihydro-2(3H)-Furanone

Sodium hydroxide (65 g, 1.625 moles) in 65 g $H_2O$ was added over a period of one hour to a stirring solution of ethyl acetoacetate (192 g, 1.47 moles), 1,2-butylene oxide (120 g, 1.66 moles) and $H_2O$ (470 g) in a two liter, four-neck flask equipped with a mechanical stirrer, thermometer, addition funnel, and condenser. The reaction was run at about 25° C. for three hours. The mixture was transferred to a separatory funnel and acidified with 155 g 20° Baume hydrochloric acid. The organic fraction (182.6 g) was placed on a Rotovap and stripped at 60° C. and 15 torr to yield 151.8 g residue and 29.5 g distillate. The main fraction (151.8 g) and a methylene chloride extract (32 g) of the aqueous phase were distilled using a Raschig ring packed column and a Perkins Triangle Head as in Example I. Three fractions were obtained upon distillation. Fraction 1 contained mostly unreacted ethyl acetoacetate. Fraction 2 (7.6 g) had a boiling point of 90–100° C. at 2 torr and contained 86.6% of the desired furanone product. Fraction 3 (88.3 g) boiled in the range 100–160° C. at 2 torr and contained 93.4% lactone. Total yield of lactone was 90.4 g or 39.3%.

EXAMPLE VII

Preparation of 3-Acetyl-5-Ethyldihydro-2(3H)-Furanone

Sodium hydroxide (64 g, 1.6 moles) in 64 g H₂O was added over a period of 50 minutes to a stirring solution of t-butyl acetoacetate (249 g, 1.5 moles), 1,2-butylene oxide.(108 g, 1.5 moles) and H₂O (217 g) in a one liter, four-neck flask equipped with addition funnel, thermometer, mechanical stirrer, and condenser. The reaction was run at about 25° C. for 10 hours. The mixture was transferred to a separatory funnel and acidified to a pH of 6 with 31% hydrochloric acid.

The organic phase (321.7 g) was distilled as in the preceding examples yielding four fractions. Fraction 4 (boiling point 90–120° C. at 1 torr) yielded 158.6 g of the desired lactone. Fractions 1–3 were comprised principally of t-butyl alcohol and unreacted starting materials in addition to a small amount of lactone. Total yield of lactone was 155.1 g or 66.3%. Conversion of the 1,2-butylene oxide was 97.0% with a selectivity of 68.4% to the desired furanone product. The improvement obtained when the base is added to a mixture of the epoxide, beta-ketoester and water is readily apparent when one compares the yield obtained from this example with the yields obtained in Examples I—III which ranged from 42% to only as high as 57%.

EXAMPLE VIII

Preparation of 3-Acetyl-5-Ethyldihydro-2(3H)-Furanone

Sodium hydroxide (82.5 g, 205 moles) in 82.5 g H₂O was added over a period of 65 minutes to a stirring solution of n-butylacetoacetate (308.6 g, 1.875 moles), 1,2-butylene oxide (108 g, 1.5 moles) and H₂O (102 g) in a one liter, four-neck flask equipped with a thermometer, mechanical stirrer, addition funnel, and condenser. The reaction was stirred at about 25° C. for 10 hours. The mixture was transferred to a separatory funnel and acidified with 31% hydrochloric acid to pH 6. The organic phase and aqueous phase separated cleanly. The organic phase (377 g) was distilled as in the preceding examples to obtain three fractions with fraction 3, boiling point 110° C.–120° C., yielding 151.9 g lactone when analyzed by gas chromatography. Fractions 1 and 2 comprised principally butyl alcohol and unreacted starting materials in addition to a small amount of lactone. Total yield of lactone was 150.4 g or 64.2%. 1,2-Butylene oxide conversion was 87.0% with a selectivity to the desired furanone of 77.3%.

EXAMPLE IX

Preparation of 3-Acetyl-5-Ethyldihydro-2(3H)-Furanone

To demonstrate the ability to obtain even higher yields with the process of the present invention by utilizing the preferred beta-diketoesters wherein the ester moiety is derived from a higher branched-chain alcohol, the following experiment was conducted. For the reaction, 2-ethylhexyl acetoacetate (338.4g 1.423 moles) 1,2-butylene oxide (85.4g, 1.186 moles) and 140.4g distilled water were combined in a reactor equipped with a mechanical stirrer, agitator, addition funnel, condenser, ice bath and thermometer. The mixture was cooled to 20° C. while agitating and a solution of 59.8g sodium hydroxide (1.491 moles) in 59.8g distilled water was added dropwise over a period of 35 minutes. The maximum temperature of the mixture during the addition was 34° C. The mixture was then stirred for 13½ hours at a temperature from 25° C. to 31° C. while following the reaction by gas chromatography. When the reaction was essentially complete, 123.5 mls concentrated hydrochloric acid was added to bring the mixture to a pH of 5. Agitation was stopped and the organic and aqueous phases allowed to separate. The organic phase was recovered and heated under vacuum to remove the 2-ethylhexanol. 185 Grams of the desired lactone product was obtained (72.4% yield). Conversion of the 1,2-butylene oxide was 90.6% with a selectivity to the desired lactone of 79.9%.

EXAMPLE X

Preparation of 3-Acetyl-5-Ethyldihydro-2(3H)-Furanone

Similar to the procedure in Example IX, isooctyl acetoacetate (338.4g, 1.423 moles), 1,2-butylene oxide (85.4 g, 1.186 moles) and 140.4 g distilled water were charged to a reactor and agitated. To this mixture a solution of 59.8 g sodium hydroxide (1.494 moles) and 59.8 g distilled water was added dropwise over a period of about 18 minutes while maintaining the temperature at 20° C. to 30° C. The mixture was then allowed to stir at a temperature from 25° C. to 32° C. for 13 hours, after which time 123.5 mls concentrated hydrochloric acid was added. The organic phase was separated from the water phase and the unreacted materials and isooctyl alcohol removed by vacuum distilling using a packed column. 140.5 Grams of the desired lactone product was obtained (76.0% yield). Conversion of the butylene oxide was 77.7% with a selectivity to the desired lactone of 97.9%.

EXAMPLE XI

Preparation of 3-Acetyl-5-Propyldihydro-2(3H)-Furanone n-Octyl acetoacetate (313.3 g, 1.42 moles), 1,2-pentylene oxide 101.8 g, 1.18 moles) and 157.5 g distilled water were combined in a reactor. A solution of 59.6 g sodium hydroxide (1.49 moles) in 59.6 g distilled water was added over a one-hour period while maintaining the temperature in the range of 22 to 26° C. The reaction mixture was then allowed to stir for an additional 11½ hours while maintaining the temperature between 28° C. and 36° C. The reaction mixture was then acidified to pH 5.8 by the addition of concentrated hydrochloric acid. After separation of the organic and aqueous phases, the organic layer was stripped under reduced pressure to remove the n-octanol and any unreacted n-octyl acetoactetate. 3-Acetyl-5-propyldihydro-2(3H)-furanone

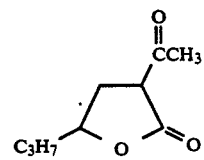

was recovered upon distillation in 62.4% yield.

EXAMPLE XII

Preparation of 3-Acetyl-5-Butyldihydro-2(3H)Furanone n-Butyl acetoacetate (1214 g, 7.6 moles), 1,3-hexylene oxide (640 g, 6.4 moles) and 590 g water were charged to a reactor and agitated. A solution of 322 g sodium hydroxide (8.1 moles) in 322 g water was then slowly added over a 30-minute period while maintaining the temperature of the mixture between 26° C. and 29° C. The reaction was continued for 10 hours and 830 g concentrated hydrochloric acid then added to adjust the pH to 6.8. The aqueous and organic phases were allowed to separate and the recovered organic layer stripped under reduced pressure to remove n-butanol and any unreacted n-butyl acetoacetate. 3-Acetyl-5-butyldihydro-2(3H)-furanone

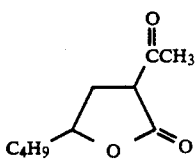

was recovered by distillation in 58.1% yield Conversion of the 1,2-hexylene oxide was 75.9% with a selectivity to the desired furanone of 76.6%.

We claim:

1. A process for preparing substituted furanones which comprises combining a 1,2-epoxyalkane containing from 3 to 6 carbon atoms, a beta-ketoester of the formula

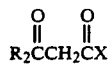

where $R_2$ is a $C_{1-4}$ alkyl group and X is a $C_{4-10}$ alkoxy group, and water; adding aqueous sodium hydroxide or potassium hydroxide with agitation at a rate such that the temperature of the reaction mixture does not exceed 40° C., said reaction mixture containing 20% to 60% water and 2% to 4% molar excess of the base based on the beta-ketoester, with the molar ratio of the 1,2-epoxyalkane to beta-ketoester ranging from 1:1.1 to 1:1.7; maintaining the temperature of the mixture from 20° C. to 35° C. until the reaction is essentially complete; adding mineral acid to adjust the pH to between 4 and 7; separating the organic phase from the aqueous phase; and recovering a substituted furanone product of the formula

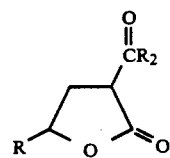

wherein R is a $C_{1-4}$ alkyl group and $R_2$ is the same as defined above from the organic phase.

2. The process of claim 1 wherein the 1,2-epoxyalkane is 1,2-butylene oxide.
3. The process of claim 1 wherein the 1,2-epoxyalkane is 1,2-pentylene oxide.
4. The process of claim 1 wherein $R_2$ is methyl.

* * * * *